United States Patent [19]

Gradeff et al.

[11] 4,041,083
[45] Aug. 9, 1977

[54] PROCESS FOR THE SELECTIVE HYDROGENATION OF THE KETO GROUP IN NONCONJUGATED OLEFINIC KETONES

[75] Inventors: Peter S. Gradeff, Andover; Giuseppe Formica, Piscataway, both of N.J.

[73] Assignee: Rhodia, Inc., New York, N.Y.

[21] Appl. No.: 728,346

[22] Filed: Sept. 30, 1976

[51] Int. Cl.$^2$ .............................................. C07C 29/00
[52] U.S. Cl. ........................... 260/617 C; 260/586 P; 260/590 R; 260/591; 260/592; 260/593 R; 260/618 H; 260/631 H; 260/631.5; 260/638 B
[58] Field of Search .......... 260/617 C, 618 H, 631 H, 260/631.5, 638 B

[56] References Cited

U.S. PATENT DOCUMENTS

| | | | |
|---|---|---|---|
| 2,009,948 | 7/1935 | Schmidt et al. | 260/638 B |
| 2,448,047 | 8/1948 | Peppel | 260/618 H |
| 2,767,221 | 10/1956 | Ballard et al. | 260/638 B |
| 2,983,734 | 5/1961 | Sargent | 260/347.8 |
| 3,102,150 | 8/1963 | Hunter et al. | 260/638 B |
| 3,109,865 | 11/1963 | Foreman | 260/638 B |
| 3,268,589 | 8/1966 | Rowland | 260/617 C |
| 3,284,517 | 11/1966 | Rylander et al. | 260/618 H |
| 3,463,818 | 8/1969 | Blumenthal | 260/638 B |
| 3,471,575 | 10/1969 | Kuch et al. | 260/638 B |
| 3,655,777 | 4/1972 | Rylander et al. | 260/638 B |
| 3,686,333 | 8/1972 | Duyverman | 260/638 B |
| 3,937,723 | 2/1976 | Schulte-Elte | 260/617 C |
| 3,953,524 | 4/1976 | Steiner | 260/638 B |
| 3,980,718 | 9/1976 | Shabtai et al. | 260/638 B |
| 3,991,127 | 11/1976 | Corr et al. | 260/638 B |

OTHER PUBLICATIONS

"Chem. Abstracts," vol. 41, p. 109, (1947).
Adams et al., "J. A. C. S.," vol. 79, p. 169, (1957).

*Primary Examiner*—Norman Morgenstern

[57] ABSTRACT

A process is provided for the selective hydrogenation of the keto group of selected nonconjugated ketones in the presence of chromium-promoted Raney nickel, a strong base selected from the group consisting of alkali metal hydroxides and alcoholates, and methanol or ethanol, with, preferably, a small amount of water, and a small amount of nitrogen base, such as ammonia or an amine.

16 Claims, No Drawings

PROCESS FOR THE SELECTIVE HYDROGENATION OF THE KETO GROUP IN NONCONJUGATED OLEFINIC KETONES

Although viewed as a difficult problem (Chemtech, June, 1975, p. 382), selective hydrogenations of unsaturated aldehydes to unsaturated alcohols have been achieved in several instances using a variety of catalytic systems, and are well reported. The case of unsaturated ketones is quite different. Rylander in *Catalytic Hydrogenation over Platinum Metals* (Academic Press, 1967, p. 271) has indicated that "generally hydrogenation of an unsaturated olefinic ketone proceeds with preferential saturation of the olefinic function." There are indeed very few exceptions: one is an $\alpha,\beta$-unsaturated ketone

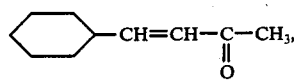

reportedly hydrogenated to

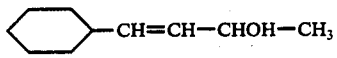

in the presence of colloidal Pd and promoters (*Chemical Abstracts*, 41 (1947), p. 109) and another tetrasubstituted olefinic ketone, ethyl 2,3-dimethyl-5-carbethoxy-6-one-2-heptenoate:

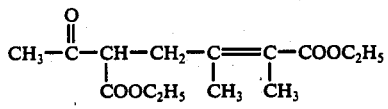

converted to the corresponding unsaturated carbinol using platinum oxide in ethanol (R. Adams and M. Gianturco, *J. Am. Chem. Soc.* 79 (1957), p. 169).

Reduction of methyl heptenone

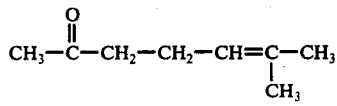

and homologues to the corresponding secondary unsaturated alcohols, which are desirable ingredients for perfumery and intermediates for syntheses, is presently done primarily by the aluminum isopropylateisopropanol method, as none of the known catalytic hydrogenation processes appears applicable. The platinum oxide/ethanol indicated by Adams and Gianturco, the palladium, ruthenium and nickel on carbon, the Raney nickel, the chromium- and cobalt-promoted Raney-nickels and other widely used catalytic systems, all are unsuccessful.

In accordance with the present invention, it has been discovered that a catalytic system comprising chromium-promoted Raney nickel, a strong base selected from the group consisting of alkali metal hydroxides and lower alcoholates, and methanol or ethanol, directs preferential hydrogenation of the keto group in a limited class of unsaturated ketones, including methyl heptenone and selected homologues. The olefinic group is sterically hindered, and contains at most one hydrogen; thus, it can be trisubstituted, or tetrasubstituted. The keto group is sterically nonhindered, and may tolerate only a limited substitution, as defined in the general formula:

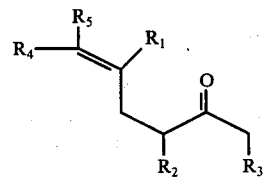

wherein:

$R_1$ is selected from the group consisting of hydrogen, methyl and ethyl;

$R_1$ can be taken together with $R_4$ or $R_5$ to form an unsaturated cycloaliphatic ring, with the olefinic group in the ring;

$R_2$ is selected from the group consisting of hydrogen; and, when $R_3$ is hydrogen, methyl;

$R_3$ is selected from the group consisting of hydrogen; and, when $R_2$ is hydrogen, methyl, ethyl and phenyl;

$R_2$ and $R_3$ can be taken together to form a six-membered saturated cycloaliphatic ring comprising the keto group;

$R_4$ and $R_5$ are selected from the group consisting of alkyl, aryl, alkaryl, aralkyl, cycloalkyl, alkcycloalkyl and cycloalkalkyl, having from one to about 20 carbon atoms; and $R_4$ and $R_5$ can be taken together to form a cycloaliphatic ring attached to the olefinic group.

Accordingly, the process of the invention comprises selectively hydrogenating the keto group of such nonconjugated olefinic ketones in the presence of hydrogen; chromium-promoted Raney nickel; a strong base selected from the group consisting of alkali metal hydroxides and alcoholates; and a lower alkanol having from one to two carbon atoms. Preferably, a small amount of water and a small amount of a nitrogen base such as ammonia or an amine are also present, since they effectively increase the rate of hydrogenation.

The chromium-promoted Raney nickel is known, and is available commercially. It can be obtained by alkaline digestion of the commercially available alloy of nickel aluminum and chromium.

Chromium-promoted Raney nickel containing chromium in an amount within the range from about 0.5 to about 20% by weight is effective. Preferably, the chromium content is within the range from about 1 to about 10%.

The active chromium-promoted Raney nickel can be used without a support, but if desired, a suitable inert support can be used. Such supports are also conventional, and include, for example, carbon, silica gel, barium, charcoal, calcium carbonate, aluminum sulfate, and kieselguhr.

The chromium-promoted Raney nickel can be purchased already activated, i.e., most of the aluminum digested by one of the standard procedures. Prior to use most of the water is decanted, and the wet catalyst employed as such.

In the absence of strong base and methanol or ethanol, chromium-promoted Raney nickel is inactive, as also is the plain Raney nickel. When the strong base and methanol or ethanol are present, chromium-promoted Raney nickel is active, but Raney nickel is not.

An amount of strong base within the range from about 0.05 to about 5 grams per mole of ketone is added to the chromium-promoted Raney nickel. A larger amount than 5 grams can be used, but does not give any improvement in the catalytic effect. Normally, an amount of base within the range from about 0.1 to about 0.5 g per mole of ketone is employed, since these amounts give good selectivity and good conversions.

Surprisingly, only the very strong bases, i.e., the alkali metal hydroxides and alcoholates, are effective. The alkali metal alcoholates of alcohols having from one to about 30 carbon atoms can be used. Usually, alcoholates of the higher alcohols having from six to 30 carbon atoms can be used because in the presence of methanol or ethanol, they will ultimately revert to the lower alcoholate. Weak bases are not effective.

The alkali can be added to the reaction mixture as a solid, or in solution in water, methanol or ethanol.

Methanol or ethanol are integral parts of the catalytic system. The reactions where methanol or ethanol is omitted are very slow, or do not proceed at all, and the selectivity of the hydrogenation of the keto group is quite poor. Ethanol is not as effective as methanol, giving a slower reaction rate, although it does give good selectivity. Surprisingly, alcohols higher than ethanol are ineffective, resulting in very poor yields; only a few percent of ketone is hydrogenated in the presence of n-propyl and isopropyl alcohols, for example.

The reaction does not proceed with other conventional inert solvents, such as benzene and tetrahydrofuran.

The amount of methanol and/or ethanol is also important to obtain a satisfactory hydrogenation rate and good selectivity. For example, 20 ml of methanol per mole of ketone gives only a negligible reaction. An effective amount of methanol and/or ethanol is within the range from about 25 to about 250 ml per mole of ketone. Preferably, the amount is within the range from 40 to about 150 ml per mole of ketone.

It is surprising that a small amount of water also increases the hydrogenation rate. In the absence of water, i.e., in essentially anhydrous reaction mixture, good selectivity is obtained, but a relatively slow reaction. Thus, in an anhydrous system, after 22 hours of reaction, although selectivity was good, there was still about 17% ketone remaining unreacted. On the other hand, in the presence of an amount within the range from about 1 to about 5% of water, based on the weight of the reaction mixture, the reaction rate is good and so is the selectivity.

An excessive amount of water also lowers the reaction rate. When the amount of water present in the reaction mixture is increased to the range of about 5 to about 8%, the reaction rate is as slow as in the case of an anhydrous system. Accordingly, it is preferred that the amount of water be less than 5%, and within the range from about 1 to about 3%.

A nitrogen base also increases the reaction rate, although it does not apparently improve selectivity. Effective nitrogen bases include ammonia, amines, and quaternary ammonium hydroxides. Aliphatic, cycloaliphatic, aromatic and heterocyclic mono and poly amines and quaternary ammonium hydroxides can be used. The strength of the nitrogen base does not appear to be critical. Weak bases such as aniline are as effective as strong bases, such as the lower aliphatic monoamines and diamines and quaternary ammonium hydroxides.

Exemplary amines which can be used include cyclohexyl amine, cyclohexylene diamine, cyclopentyl amine, dicyclopentylene diamine, methyl amine, dimethyl amine, trimethyl amine, ethyl amine, diethyl amine, triethyl amine, propyl amine, dipropyl amine, tripropyl amine, butyl amine, dibutyl amine, tributyl amine, monoethanolamine, diethanol amine, triethanolamine, aniline, ortho-, meta- and para-toluidine, ethylene diamine, diethylene triamine, triethylene tetramine, pyridine, piperidine, pyrazine, piperazine, morpholine, and quaternary ammonium hydroxides such as tetramethyl quaternary ammonium hydroxide, trimethyl benzyl quaternary ammonium hydroxide and pyridinium hydroxide.

The amount of nitrogen base can be within the range from about 0.05 to about 15 grams per mole of ketone. Although larger amounts than 15 grams can be used, a proportionate enhancement of the reaction rate is not noted. Preferably, the amount of nitrogen base is within the range from about 1 to about 5 g per mole of ketone.

Exemplary ketones to which the process of the invention is applicable include the following:

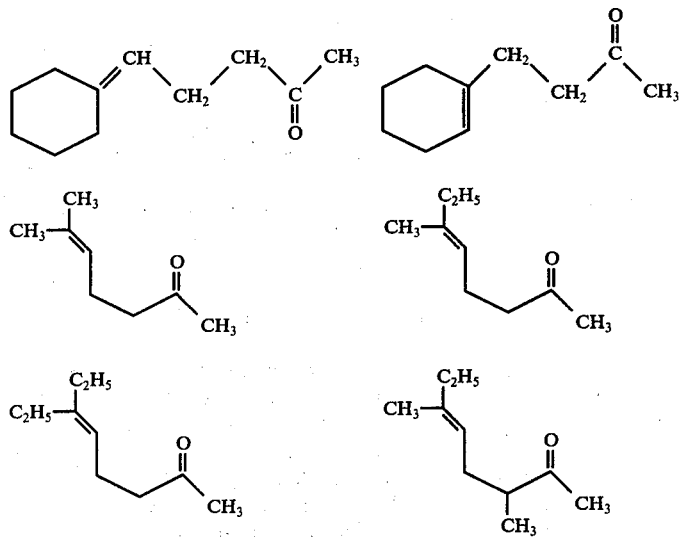

-continued

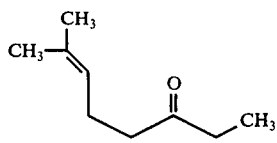
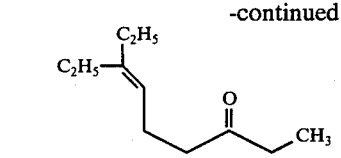

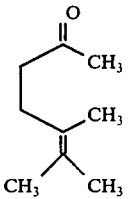

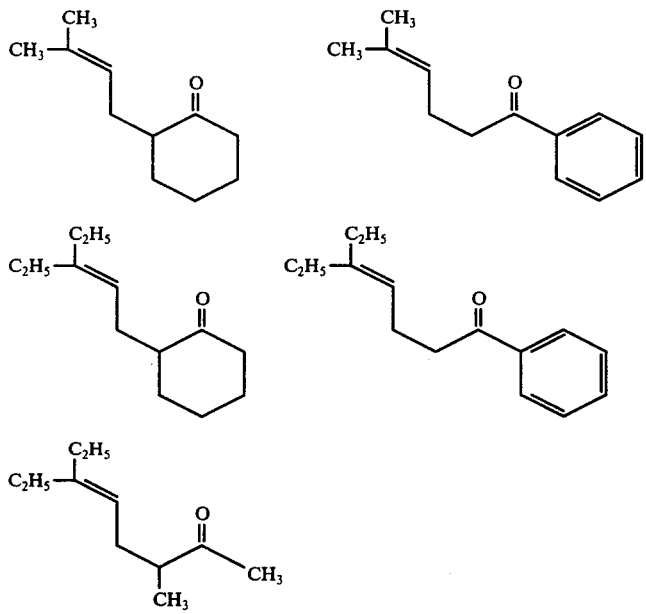

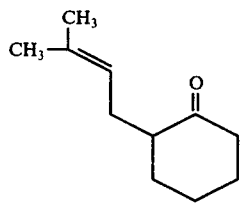

Mixture of:

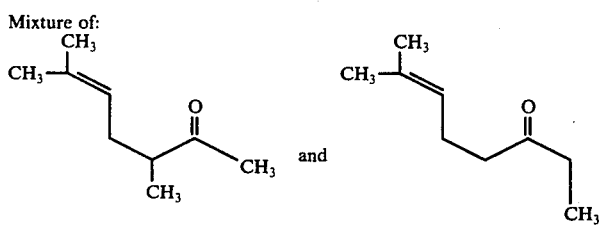

and

A small amount of the chromium-promoted Raney nickel is quite sufficient. The larger the amount of it is used, the more rapid the rate of hydrogenation.

Satisfactory results are obtained with amounts as small as 1% by weight of the ketone thereof; in some cases, amounts as small as 0.5% by weight can be used.

Normally, an amount in excess of about 25% by weight of the ketone is not required, and in most cases, an amount within the range from about 2 to about 15% by weight is preferred.

It is well known that freshly-prepared chromium-promoted Raney nickel catalysts are more active than catalysts that have been stored for some time.

The reaction can be carried out at from about 5° C to about room temperature, but is faster at elevated temperatures. There is no upper limit on reaction temperature, except that imposed by the stability of the starting ketone and/or the unsaturated alcohol reaction product. Temperatures from about 20° up to about 100° C are preferred, but the reaction temperature may in some cases be as high as 200° C.

The reaction proceeds rather rapidly, depending upon temperature, hydrogen concentration, and catalyst concentration. Usually, the reaction does not require more than 48 hours for completion, and depending upon the end product desired, may be complete in as little as one-half hour. Usually, from four to twelve hours are sufficient.

The reaction can be begun by charging the ketone, the base, the amine, the lower alkanol, and the chromium-promoted Raney nickel into a suitable pressure vessel equipped with stirring and optionally with heating or cooling facilities. After appropriate purging of the system, a hydrogen atmosphere is then provided, and hydrogen supplied to the system under pressure for a time sufficient to produce the desired reaction product.

In a preferred operative procedure, the chromium-promoted Raney nickel is stirred for a few minutes with the base, the amine and some of the alcohol, and then added to the autoclave. containing the ketone and the rest of the alcohol.

As the amount of unsaturated alcohol increases, small amounts of saturated alcohol tend to be formed, and consequently if this impurity is not desired, it is well to halt the hydrogenation at a stage before the saturated alcohol begins to be formed.

The reaction time required to reach the desired reaction product depends on a number of factors, including for example the amount and reactivity of the catalyst ingredients, the pressure, the temperature, and the desired composition of the final product. Consequently, the reaction conditions best adapted for a particular objective are normally determined by trial and error, but will be found to lie within the above parameters.

ide in methanol; and 5 g of triethylamine, were placed in a stainless steel autoclave. The reactor was purged of air, and pressurized with hydrogen to 40 psi. Agitation of the autoclave was then begun at room temperature, and samples were taken at the times indicated in Table I below. The samples were analyzed by gas liquid chromatography (GLC) for unreacted ketone (a) and the three possible mixtures of reaction products, the saturated ketone (b), the saturated alcohol (c), and the unsaturated alcohol (d) (which was the desired product, representing selective hydrogenation of the keto group to the exclusion of the olefinic group). The following results were obtained:

TABLE I

| COMPONENTS | % of Components after Hydrogenation by GLC Analysis After Hours | | | | | |
|---|---|---|---|---|---|---|
| | 1½ | 3 | 4½ | 6 | 7½ | 9 |
| (a) Unreacted ketones | 56.9 | 31.1 | 16.0 | 7.8 | 4.9 | 4.1 |
| (b) Saturated ketones | 1.7 | 2.8 | 2.4 | 2.2 | 2.1 | 1.8 |
| (c) Saturated alcohols | Trace | 0.9 | 2.9 | 3.5 | 4.5 | 6.1 |
| (d) Unsaturated alcohols | 41.4 | 65.2 | 78.7 | 86.5 | 88.5 | 88 |

It is normally preferred to operate the process in a manner so as to halt the hydrogenation before saturated alcohol begins to be formed in significant quantity. However, the time selected for halting the hydrogenation will of course depend upon the other parameters chosen.

It is possible to carry out the hydrogenation reaction at atmospheric pressure. However, the hydrogenation reaction then proceeds rather slowly. A suitable reaction rate is obtained at from 2 to 5 psi hydrogen pressure. The higher the hydrogen pressure, the more rapid the hydrogenation. Consequently, hydrogen pressures during the reaction of 10 psi and higher are preferred. Preferably, the hydrogen pressure in the reaction vessel is within the range from about 40 to about 100 psi, but higher pressures can be used, if desired. There is in fact no upper limit except as may be imposed by practicality, and the pressure vessels available. A suggested upper limit is 200 psi.

The following Examples in the opinion of the inventors represent preferred embodiments of the invention.

In all the Examples reported below, the reactions were carried out either in a stainless-steel autoclave or in a PARR Hydrogenator (a 200 ml glass reactor shaker-type apparatus designed to operate at from 0 to 60 psi pressure). The progress of the hydrogenation was followed by taking samples at the intervals indicated.

EXAMPLE 1

A mixture of 3,6-dimethyl-5-heptene-2-one and 7-methyl-6-octene-3-one 140 g; chromium-promoted Raney nickel 4 g, in suspension in 5 g of water, 56 g methanol; 4.5 g of a 10% solution of potassium methox- The results show an excellent yield of unsaturated alcohols (d) after 6 hours of reaction, which was not materially improved in 3 hours further reaction. Selectivity was quite good, as evidenced by the relatively small proportion of saturated ketones, the nonselectively hydrogenated byproducts, and saturated alcohols, the fully hydrogenated byproduct.

In a continuous hydrogenation process, it would be possible to withdraw the reaction mixture after a three-hour dwell time in the reactor, and recycle the unreacted ketones for further reaction, since at this reaction stage the proportion of saturated alcohol is at a minimum, and therefore loss of the starting material in this byproduct would be substantially eliminated.

It is also apparent from the results that saturated ketones are converted to saturated alcohols in later stages of the reaction.

In contrast with the above results, the use in substitution for potassium methoxide by the bases listed in Table II gives both poor yields and poor selectivity. In experiments carried out exactly as the above, with the only change being the substitution of the base indicated, the following results were obtained:

TABLE II

| Control No. | Base | g/mol | Reaction Time (hours) | % of Components after Hydrogenation by GLC Analysis[3] | | | |
|---|---|---|---|---|---|---|---|
| | | | | a | b | c | d |
| F | LiOH | 1.0 | 3¼ | 7.0 | 8.1 | 15.2 | 69.7 |
| G[1] | — | — | 2½ | 9.0 | 20.4 | 23.0 | 47.5 |
| H[2] | — | — | 3 | 18.3 | 14.5 | 11.9 | 55.3 |
| J | (CH$_3$)$_4$NOH | 1.0 | 4 | 33.7 | 14.3 | 5.0 | 46.9 |
| K | Na$_2$CO$_3$ | 1.0 | 16 | 7.8 | 25 | 26.2 | 41.0 |
| L | Borax | 1.0 | 3½ | 17.2 | 27.9 | 16.2 | 38.7 |

[1] 8g cat/mol
[2] 4g cat/mol
[3] see Table I for meaning of a, b, c and d

It is apparent from the above results that lithium hydroxide is not acceptable. Poor selectivity and/or a poor reaction rate are obtained with it and the other alkalis. In fact, the results with the other bases are no better than the results obtained in the absence of base, Controls G and H. In all cases, selectivity is unacceptable.

EXAMPLE 2

A mixture of 3,6-dimethyl-5-heptene-2-one and 7-methyl-6-octene-3-one, 140 g: chromium-promoted Raney nickel 4 g in suspension in 5 g of water: 56 g methanol and 4.5 g of a 10% solution potassium methoxide in methanol were placed in a stainless-steel autoclave. The system was purged of air and pressurized with hydrogen to 40 psi. Agitation of the autoclave was then begun at room temperature and samples were taken at the times indicated in Table III below. The samples were analyzed by gas liquid chromatography (GLC) for unreacted ketone (a) and the three possible reaction products, the saturated ketone (b), the saturated alcohol (c) and the unsaturated alcohol (d) (which was the desired product, representing selective hydrogenation of the keto group to the exclusion of the olefinic group). The following results were obtained:

TABLE III

| | % of Components after Hydrogenation by GLC Analysis After Hours[3] | | | | |
|---|---|---|---|---|---|
| COMPONENTS | 3 | 6½ | 25 | 33 | 49 |
| (a) Unreacted ketones | 69.4 | 53.4 | 12.1 | 7.7 | 4.9 |
| (b) Saturated ketones | 1.8 | 2.8 | 3.2 | 3.1 | 2.6 |
| (c) Saturated alcohols | — | — | 4.7 | 4.7 | 7.3 |
| (d) Unsaturated alcohols | 28.7 | 43.6 | 80.0 | 84.5 | 85.1 |

[3]see Table I for meaning of a, b, c, and d

The results show an excellent yield after 6 hours of reaction, which was not materially improved in 3 hours further reaction. Selectivity was quite good, as evidenced by the relatively small proportion of saturated ketones and saturated alcohols, the fully hydrogenated and non-selectively hydrogenated byproducts. In the absence of the amine, reaction rate was slower than in Example 1.

In a continuous hydrogenation process, it would be possible to arrest the reaction shortly, and recycle the unreated ketones for further reaction, since before this reaction stage the proportion of saturated alcohol is at a minimum, and therefore loss of the starting material in this byproduct would be substantially eliminated. It is apparent from the results that saturated ketones are converted to saturated alcohols in later stages of the reaction.

These results show that the presence of amine is quite beneficial in increasing the reaction rate although not affecting the selectivity. However, good yields are obtained after the longer reaction time.

EXAMPLES 3 TO 8

A mixture of 3, 6-dimethyl-5-heptene-2-one and 7-methyl-6-octene-3-one, 140 g; chromium promoted Raney nickel 4 g in suspension in 5 g of water: the amount of alcohol listed below in Table IV; 4.5 g of a 10% solution of potassium methoxide in methanol and 5 g of triethylamine were placed in a stainless steel autoclave. The system was purged of air and pressurized with hydrogen to 40 psi. Agitation of the autoclave was then begun at room temperature, and reaction continued for the time indicated in Table IV below. The products were analyzed by gas liquid chromatography (GLC) for unreacted ketone (a), and the three possible reaction products the saturated ketone (b) the saturated alcohol (c), and the unsaturated alcohol (d) (which was the desired product, representing selective hydrogenation of the keto group to the exclusion of the olefinic group). The following results were obtained:

| Example or Control No. | Solvent | ml/mol | Reaction Time (hrs) | % of Components after Hydrogenation by GLC Analysis After Hours[3] | | | |
|---|---|---|---|---|---|---|---|
| | | | | a | b | c | d |
| 3 | Methanol | 4 | 7 | 97.6 | 1.8 | Trace | Trace |
| | | | 22½ | 97.6 | 1.8 | Trace | Trace |
| 4 | Methanol | 20 | 20 | 96 | 1.3 | Trace | Trace |
| 5 | Methanol | 35 | 23 | 64.0 | 2.0 | Trace | 31.7 |
| 6 | Methanol | 50 | 7 | 32.9 | 3.2 | 1.2 | 60.2 |
| | | | 14 | 2.0 | 1.9 | 11.7 | 82 |
| 7 | Methanol | 140 | 1½ | 31.4 | 9.5 | 4.2 | 53.3 |
| | | | 3½ | 5.4 | 7.9 | 14.5 | 68.1 |
| 8 | Ethanol | 70 | 14½ | 35.3 | 4.0 | 1.4 | 57.7 |
| Control | | | | | | | |
| A | n-Butanol | 70 | 7 | 97.2 | 0.9 | — | 0.3 |
| B | iso-Butanol | 70 | 21 | 94.5 | 1.1 | — | 2.7 |
| C | n-Propanol | 70 | 21 | 95.4 | 0.9 | — | 1.9 |
| D | Tetrahydrofuran | 70 | 3 | 98.3 | 0.7 | — | 1.0 |
| E | Benzene | 70 | 16 | 86.7 | 6.1 | — | 7.2 |

[3]see Table I for meaning of a, b, c and d

The above results show that the methanol and ethanol definitely contribute to selectivity and increase the reaction rate. In Controls A to E, in the presence of n- and iso-butyl alcohol, and n-propyl and isopropyl alcohol, tetrahydrofuran and benzene, the reaction rate is virtually negligible, and nearly all of the starting ketone is recovered unreacted.

The results for Examples 3 to 7 also show that the influence of the methanol is proportionate to the amount. In amounts below 25 ml per mole, the methanol also was virtually ineffective, no better than the higher alcohols in the Controls. At amounts within the range from 35 to 140 ml per mole, a good reaction rate is obtained (Examples 5 to 7). The same is true of ethanol, in the proportion of 70 ml per mole, as shown in Example 8.

EXAMPLES 9 AND 10

A mixture of 3,6-dimethyl-5-heptene-2-one and 7-methyl-6-octene-3-one 140 g; chromium-promoted Raney nickel 4g, 56 g methanol, 4.5 g of a 10% solution of potassium methoxide in methanol, 5 g of triethylamine and the amount of water noted in Table V were placed in a stainless-steel autoclave. The reactor was purged of air and pressurized with hydrogen to 40 psi. Agitation of the autoclave was then begun at room temperature, and reaction continued for the times indicated in Table V below. The products were analyzed by gas liquid chromatography (GLC) for unreacted ketone (a), and the three possible reaction products, the saturated ketone (b), the saturated alcohol (c), and the unsaturated alcohol (d) (which was the desired product, representing selective hydrogenation of the keto group to the exclusion of the olefinic group). The following results were obtained:

TABLE V

| Ex. No. | Water g/mole | Reaction Time (hrs) | % of Components after Hydrogenation by GLC Analysis After Hours[3] | | | |
|---|---|---|---|---|---|---|
| | | | a | b | c | d |
| 1[1] | 5 | 4½ | 16.0 | 2.4 | 2.9 | 78.7 |
| | | 7½ | 4.9 | 2.1 | 4.5 | 88.5 |
| 9 | 0 | 7 | 58.0 | 2.4 | — | 36.1 |
| | | 22 | 16.8 | 5.5 | 3.6 | 71.8 |
| 10 | 15 | 4½ | 84.2 | 1.3 | — | 12.2 |
| | | 21 | 47.3 | 4.0 | 0.9 | 46.4 |

[1]from Table I (Example 1).
[3]see Table I for meaning of a, b, c and d

The above results include Example 1, to show the importance of the water in increasing the reaction rate. When no water is present, the reaction is rather slow (Example 9). When 15 g of water per mole of ketone are present, the reaction rate is even slower (Example 10). However, in each case selectivity is good. The product could be accepted in a continuous process, and the unreacted ketone recycled.

EXAMPLES 11 TO 31

A mixture of 3,6-dimethyl-5-heptene-2-one and 7-methyl-6-octene-3-one 140 g; chromium-promoted Raney nickel 4 g in suspension with 5 g of water, 70 ml methanol, and the amount and alkali and amine noted in Table VI were placed in a stainless steel autoclave. The reactor was purged of air and pressurized with hydrogen to 40 psi, or as indicated in Table VI. Agitation of the autoclave was then begun at room temperature, and reaction continued at 20° to 35° C for the times indicated in Table VI below. The products were analyzed by liquid chromatography (GLC) for unreacted ketone (a) and the three possible reaction products, the saturated ketone (b), the saturated alcohol (c), and the unsaturated alcohol (d) (which was the desired product representing selective hydrogenation of the keto group to the exclusion of the olefinic group). The following results were obtained:

TABLE VI

| Example No. | Amine/g/mole | Base/g. | Reaction Time (hrs) | % of Components after Hydrogenation by GLC Analysis After Hours[10] | | | |
|---|---|---|---|---|---|---|---|
| | | | | a | b | c | d |
| 11 | TEA[1]/5.0 | KOH/4.5 | 3 | 14.4 | 2.9 | 3.8 | 79.0 |
| | | | 18½ | 5.4 | 2.3 | 6.2 | 86.0 |
| 12 | TEA/1.0 | NaOH/1.0 | 3 | 25.8 | 5.3 | 7.1 | 61.8 |
| 13 | TEA/1.0 | KOMe°/2.0 | 5 | 5.2 | 4.0 | 9.4 | 81.3 |
| 14[2] | TEA/5.0 | KOMe°/4.5 | 4 | 3.3 | 2.4 | 7.8 | 86.5 |
| 15[3] | TEA/5.0 | " | 1½ | 54.6 | 3.4 | 0.6 | 41.4 |
| | | | 8 | 0.7 | 1.2 | 11.7 | 86.2 |
| 16 | TEA/2.0 | " | 7 | 1.2 | 1.4 | 10.4 | 86.4 |
| 17[4] | TEA/5.0 | " | 7 | 33.3 | 3.6 | 1.4 | 61.6 |
| | | | 23 | 10.1 | 3.0 | 5.0 | 81.9 |
| 18[5] | Aniline/5.0 | " | 18½ | 3.2 | 2.6 | 7.4 | 84.5 |
| 19[5] | NH₄OH/5.0 28% | " | 24 | 21.0 | 1.7 | 0.5 | 75.2 |
| 20[5] | Hexadecyl amine/5.0 | " | 16½ | 23.7 | 1.6 | 0.4 | 73 |
| 21[5] | Cyclohexyl amine/5.0 | " | 24½ | 26.2 | 1.8 | 0.2 | 69.3 |
| 22[5] | Ethylene diamine/5.0 | " | 5½ | 82.5 | 2.3 | — | 11.4 |
| 23[5] | Dimethylamine 40%/5.0 | " | 24 | 35.5 | 1.4 | — | 61.2 |
| 24 | Butylamine/5.0 | KOH/1.0 | 3½ | 84.5 | 0.8 | — | 14.5 |
| 25 | Dibutyl amine/5.0 | " | 3 | 63.9 | 4.1 | — | 31.9 |
| 26 | Tributyl amine/5.0 | " | 3 | 36.0 | 19.9 | 6.3 | 37.7 |
| 27[5] | Di-ethyl amine/5.0 | KOH/1.0 | 4 | 71.6 | 2.6 | — | 25.9 |
| 28[6] | TEA[1]/5.0 | KO-t-But./1.5 | 1½ | 15.8 | 7.9 | 9.1 | 66.3 |
| 29[7] | " | KOH/4.5 | 3 | 53.7 | 3.1 | 1.2 | 42.0 |
| 30[2] | Tributyl amine/5.0 | KOMe/4.5 | 2½ | 61.8 | 3.9 | — | 33 |
| 31[8] | Butyl amine/5.0 | " | 22 | 46.8 | 1.2 | — | 50.6 |
| Control M[9] | TEA/5.0 | KOMe/4.5 | 5 | 60.9 | 16.1 | 2.3 | 20.6 |
| Control N[9] | TEA/5.0 | " | 21 | 36.6 | 21.4 | 6.7 | 33.6 |

°KOMe = KOCH₃
[1]TEA = Triethylamine
[2]8g/mole Chromium-Raney nickel
[3]w/recycled Chromium-Raney nickel
[4]2g/mole Chromium-Raney nickel
[5]in PAAR Hydrogenator
[6]60 psi autoclave
[7]50° C 60 psi autoclave
[8]40 psi autoclave
[9]Raney nickel without chromium
[10]see Table I for meaning of a, b, c and d It is apparent from the above results that using chromium-promoted Raney nickel good yields and good selectivity are obtained using a variety of strong bases and amines over a wide range of reaction times.

In contrast Raney nickel without chromium gives very poor selectivity and a slow reaction rate.

EXAMPLES 32 TO 34

One mole of the ketone listed in Table VII below 3 g of chromium-promoted Raney nickel, 70 to 170 ml methanol 5 g of a 10% solution of potassium methoxide in methanol and 5 g of triethylamine were placed in a stainless-steel autoclave. The reactor was purged of air and pressurized with hydrogen to 40 psi. Agitation of the autoclave was then begun at room temperature, and reaction continued for the times indicated in Table VII below. The products were analyzed by gas liquid chromatography (GLC) for unreacted ketone (a), and the three possible reaction products, the saturated ketone (b), the saturated alcohol (c), and the unsaturated alcohol (d) (which was the desired product representing selective hydrogenation of the keto group to the exclusion of the olefinic group). The following results were obtained:

TABLE VII

| Example or Control No. | Ketone | Reaction Time (hrs) | % of Components after Hydrogenation by GLC Analysis After Hours[3] | | | |
|---|---|---|---|---|---|---|
| | | | a | b | c | d |
| 32 | 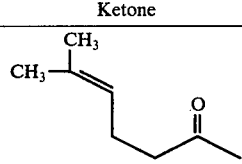 | 2.2<br>16 | 3.8<br>0.3 | 0.8<br>— | 4.4<br>15.4 | 88.5<br>82.5 |
| 33 | 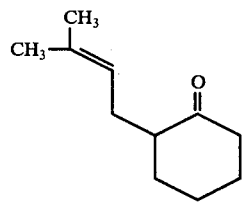 | 7<br>24 | 26.6<br>4.7 | 2.7<br>2.8 | —<br>1.6 | 69.4<br>89.3 |
| 34 | 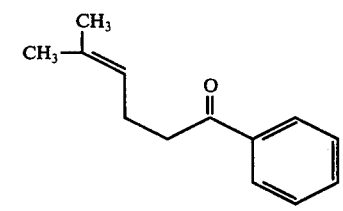 | 2.1 | 21.9 | 0.7 | 1.5 | 72.8 |
| O | 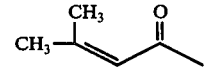 | 16 | 10 | 89.3 | — | — |
| P | 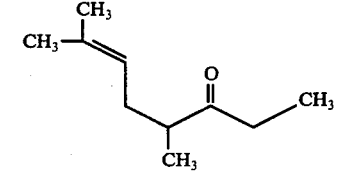 | 20.5 | 94.7 | 1.8 | 0.1 | 1.6 |
| Q | 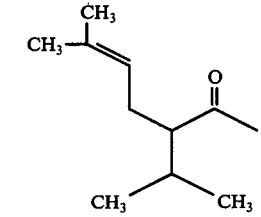 | 7 | 93 | 2.1 | — | 2.4 |
| R | 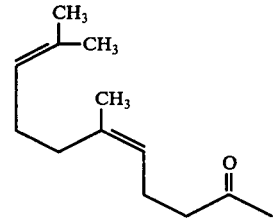 | 6<br>49[1] | 97.8<br>45.5 | 1.8<br>27.5 | 0.4<br>2.6 | —<br>24.4 |
| S | 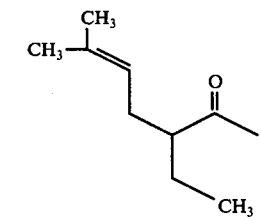 | 24 | 49.7 | 14.8 | 5.5 | 27.2 |

TABLE VII-continued

| Example or Control No. | Ketone | Reaction Time (hrs) | % of Components after Hydrogenation by GLC Analysis After Hours[3] | | | |
|---|---|---|---|---|---|---|
| | | | a | b | c | d |
| T | 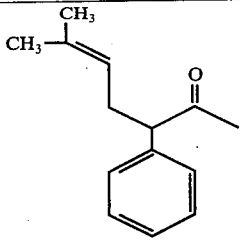 | 3 | 92.6 | 1.1 | — | 5.9 |
| | | 23.5 | 38.7 | 13.3 | 5.4 | 41.8 |
| U | 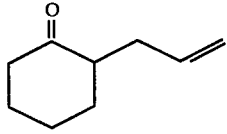 | 16 | 19.8 | 80.2 | — | — |
| | | 20 | 1.0 | 98.5 | — | 0.4 |

[1]using double the amounts of methanol and chromium-Raney nickel.
[3]see Table I for meaning of a, b, c and d.

The above data show that ketones falling within the invention Examples 32 to 34 give good results under these conditions, while the other ketones do not. The undue steric hindrance of the keto group is an interference, as shown by Controls P,Q,S and T. The effect of an unshielded double bond is shown by its preferential hydrogenation in Control U which is also the result in Control O where the double bond is $\alpha,\beta$ to the carbonyl. The Control R shows the steric effects exercised by the spatial arrangement of the relatively long carbon chain.

Having regard to the foregoing disclosure, the following is claimed as the inventive and patentable embodiments thereof:

1. A process for the preparation of olefinically unsaturated alcohols which comprises selectively hydrogenating the keto group of nonconjugated olefinic ketones having the general formula:

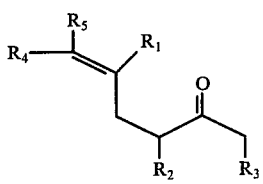

wherein
$R_1$ is selected from the group consisting of hydrogen, methyl and ethyl; and
$R_1$ taken together with one of $R_4$ and $R_5$ to form an unsaturated cycloaliphatic ring;
$R_2$ is selected from the group consisting of hydrogen, and, when $R_3$ is hydrogen, methyl;
$R_3$ is selected from the group consisting of hydrogen, and, when $R_2$ is hydrogen, methyl, ethyl and phenyl; and
$R_2$ and $R_3$ taken together to form a six-membered saturated cycloaliphatic ring comprising the keto group;
$R_4$ and $R_5$ are selected from the group consisting of alkyl, aryl, alkaryl, aralkyl, cycloalkyl, alkcycloalkyl and cycloalkalkyl, having from one to about fifty carbon atoms; and
$R_4$ and $R_5$ taken together to form a cycloaliphatic ring; in the presence of hydrogen; chromium-promoted Raney nickel prepared by alkaline digestion of the alloy of nickel aluminum and chromium and containing from about 0.5 to about 20% by weight chromium; a strong alkali selected from the group consisting of alkali metal hydroxides and alcoholates having from one to about thirty carbon atoms; and a lower alkanol having from one to two carbon atoms.

2. A process according to claim 1 in which a small amount of water is also present, effective to increase the rate of hydrogenation.

3. A process according to claim 1 in which a small amount of nitrogen base is also present, effective to increase the rate of hydrogenation.

4. A process according to claim 1 in which the chromium-promoted Raney nickel contains chromium in an amount within the range from about 1 to about 10% by weight.

5. The process of claim 1, in which the amount of chromium-promoted Raney nickel is within the range from about 0.5 to about 25% by weight of ketone.

6. The process of claim 1 in which the hydrogen is at a pressure within the range from atmospheric pressure up to about 200 psi.

7. The process of claim 1 in which the reaction is carried out at a temperature within the range from about 5° to about 200° C.

8. The process of claim 1 in which the ketone is 3,6-dimethyl-5-heptene-2-one.

9. The process of claim 1 in which the ketone is 7-methyl-6-octene-3-one.

10. The process of claim 1 in which the ketone is 6-methyl-5-heptene-2-one.

11. The process of claim 1 in which the ketone is 2-(3-methyl-2-butenyl) cyclohexanone.

12. The process of claim 1 in which the ketone is 5-methyl-4-heptenophenone.

13. The process of claim 1 in which the lower alkanol is methanol.

14. The process of claim 1 in which the alkali is potassium hydroxide.

15. The process of claim 1 in which the alkali is potassium methoxide.

16. The process according to claim 1 in which small amounts of water and nitrogen base are also present, effective to increase the rate of hydrogenation.

* * * * *